US011399794B2

(12) United States Patent
Takemoto

(10) Patent No.: US 11,399,794 B2
(45) Date of Patent: Aug. 2, 2022

(54) X-RAY CT APPARATUS AND ITS CONTROL METHOD

(71) Applicant: Hitachi, Ltd., Tokyo (JP)

(72) Inventor: Kazuma Takemoto, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 9 days.

(21) Appl. No.: 17/095,820

(22) Filed: Nov. 12, 2020

(65) Prior Publication Data

US 2021/0275125 A1    Sep. 9, 2021

(30) Foreign Application Priority Data

Mar. 3, 2020  (JP) .............................. JP2020-035561

(51) Int. Cl.
*A61B 6/00* (2006.01)
*A61B 6/03* (2006.01)
*A61B 6/04* (2006.01)

(52) U.S. Cl.
CPC ............ *A61B 6/5217* (2013.01); *A61B 6/032* (2013.01); *A61B 6/0407* (2013.01); *A61B 6/40* (2013.01); *A61B 6/4435* (2013.01); *A61B 6/503* (2013.01)

(58) Field of Classification Search
CPC ..... A61B 6/5217; A61B 6/032; A61B 6/0407; A61B 6/40; A61B 6/4435; A61B 6/503; A61B 6/505; A61B 6/54; A61B 6/5205
See application file for complete search history.

(56) References Cited

FOREIGN PATENT DOCUMENTS

| JP | 03207346 A | * | 9/1991 |
| JP | 06-095999 A | | 11/1994 |

* cited by examiner

*Primary Examiner* — Courtney D Thomas
(74) *Attorney, Agent, or Firm* — Mattingly & Malur, PC

(57) ABSTRACT

An X-ray CT apparatus enables accurate determination of a scan end position and includes a rotating plate that rotates an X-ray source and an X-ray detector, oppositely provided to the X-ray source, to detect the X-ray transmitted through and around the subject. A bed for the subject moves with respect to the rotating plate, to change a scan position; and a tomographic image is generated in the scan position based on output from the X-ray detector. A storage holds a region ratio threshold value previously determined in a scan end position. A region extraction unit extracts a predetermined region from the tomographic image generated during scanning; and a comparison determination unit determines whether or not the scan position has arrived at the scan end position based on comparison between a region ratio calculated by using the region and the threshold value.

7 Claims, 14 Drawing Sheets

X-RAY CT APPARATUS AND ITS CONTROL METHOD

CLAIM OF PRIORITY

The present application claims priority from Japanese Patent Application JP 2020-035561 filed on Mar. 3, 2020, the content of which are hereby incorporated by references into this application.

BACKGROUND OF THE INVENTION

The present invention relates to an X-ray CT (Computed Tomography) apparatus for generating a tomographic image of a subject, and more particularly, to a technique of determining whether or not a position during scanning has arrived at a scan end position to terminate the scanning.

An X-ray CT apparatus is a device to generate a tomographic image of a subject by measuring projection data as an X-ray projection image of the subject at various projection angles, and performing reconstruction calculation on the multiple projection data. The generated tomographic image is used in diagnosis of the subject or the like. From the view point of reduction of scan time and reduction of exposure of the subject, it is desirable that the projection data is measured without excess or deficiency with respect to a desired region, e.g., a region of a part to be diagnostic object.

Japanese Published Examined Patent Application No. Hei 6-95999 discloses a technique of determining, based on the result of comparison between projection data previously stored as reference data and projection data collected in a position during scanning, whether or not the position during scanning has arrived at a scan end position.

However, in Japanese Published Examined Patent Application No. Hei 6-95999, since the comparison is made between the projection data as reference data and the projection data during scanning, the scan end position is shifted in some cases. That is, when the X-ray is transmitted through the subject, the quality of radiation is hardened. In some cases, a part positioned deeper from the X-ray source becomes unclear in the projection data, and the accuracy of the scan end position determination is lowered.

SUMMARY OF THE INVENTION

The present invention provides an X-ray CT apparatus which enables accurate determination of a scan end position and its control method.

To attain the above object, the present invention provides an X-ray CT apparatus including: a rotating plate that rotates an X-ray source to emit an X-ray to a subject and an X-ray detector, oppositely provided to the X-ray source, to detect the X-ray transmitted through the subject, around the subject; a bed that the subject is placed on, and that relatively moves with respect to the rotating plate, to change a scan position; an image generator that generates a tomographic image in the scan position based on output from the X-ray detector; a storage unit that holds a region ratio threshold value previously determined in a scan end position; a region extraction unit that extracts a predetermined region from the tomographic image generated during scanning; and a comparison determination unit that determines whether or not the scan position has arrived at the scan end position based on comparison between a region ratio calculated by using the region and the threshold value.

Further, the present invention provides a control method for controlling an X-ray CT apparatus, the apparatus including: a rotating plate that rotates an X-ray source to emit an X-ray to a subject and an X-ray detector, oppositely provided to the X-ray source, to detect the X-ray transmitted through the subject, around the subject; a bed that the subject is placed on, and that relatively moves with respect to the rotating plate, to change a scan position; and an image generator that generates a tomographic image in the scan position based on output from the X-ray detector, the method including: extracting a predetermined region from the tomographic image generated during scanning; and determining whether or not the scan position has arrived at a scan end position based on comparison between a region ratio calculated by using the region and a region ratio threshold value previously determined in the scan end position.

According to the present invention, it is possible to provide an X-ray CT apparatus which enables more accurate determination of a scan end position and its control method.

DETAILED DESCRIPTION OF THE PREFERRED EMBODIMENTS

First Embodiment

Figure 1:
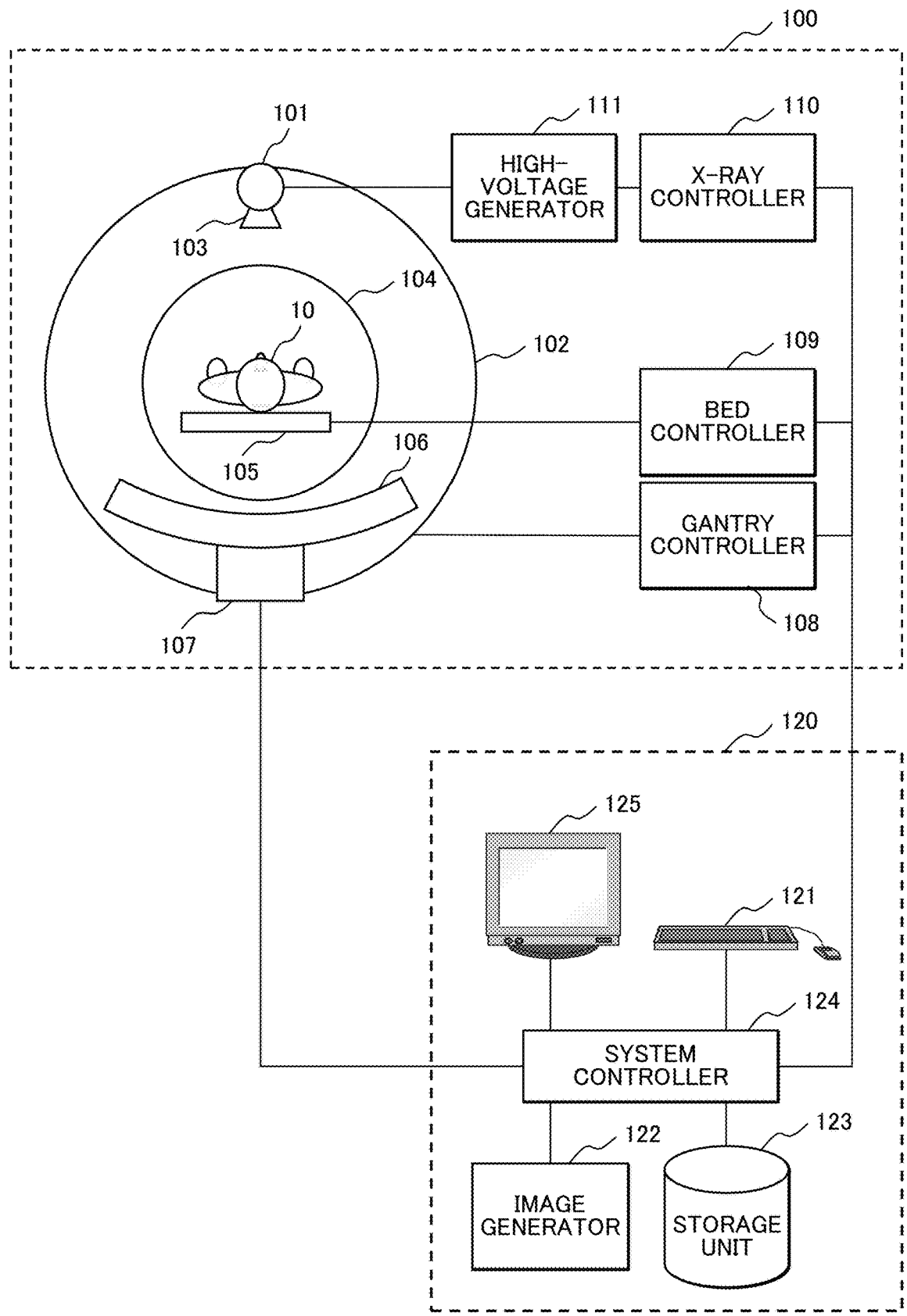
FIG. 1 is a block diagram showing an example of the entire configuration of an X-ray CT apparatus according to a first embodiment of the present invention.

Hereinbelow, preferred embodiments of an X-ray CT apparatus according to the present invention will be described in accordance with the attached drawings. Note that in the following descriptions and drawings, constituent elements having the same functional compositions will have the same reference numerals, and overlapped explanations will be omitted.

The entire configuration of the X-ray CT apparatus according to the present embodiment will be described by using FIG. 1. The X-ray CT apparatus has a scan gantry part 100 and an operation unit 120.

The scan gantry part 100 has an X-ray source 101, a rotating plate 102, a collimator 103, an X-ray detector 106, a data collection unit 107, a bed 105, a gantry controller 108, a bed controller 109, an X-ray controller 110, and a high-voltage generator 111. The X-ray source 101 is a device to irradiate a subject 10 placed on the bed 105 with an X-ray. The X-ray source 101 is, e.g., an X-ray tube. The collimator 103 is a device to limit the irradiation range of the X-ray. The rotating plate 102 has an opening 104 in which the subject 10 placed on the bed 105 enters, and has the X-ray source 101 and the X-ray detector 106. The rotating plate 102 rotates the X-ray source 101 and the X-ray detector 106 around the subject 10.

The X-ray detector 106 is provided oppositely to the X-ray source 101. The X-ray detector 106, which has multiple detection elements to detect the X-ray transmitted through the subject 10, is a device to detect spatial distribution of the X-ray. The detection elements of the X-ray detector 106 are two-dimensionally arrayed in a rotation direction and rotation axis direction of the rotating plate 102. The data collection unit 107 is a device to collect the spatial distribution of the X-ray, detected with the X-ray detector 106, as digital data.

The gantry controller 108 is a device to control rotation and tilt of the rotating plate 102. The bed controller 109 is a device to control upward-downward/forward-rearward/rightward-leftward movement of the bed 105. The high-voltage generator 111 is a device to generate a high voltage applied to the X-ray source 101. The X-ray controller 110 is a device to control output from the high-voltage generator 111. The gantry controller 108, the bed controller 109, and the X-ray controller 110 are, e.g., an MPU (Micro-Processing Unit).

The operation unit 120 has an input unit 121, an image generator 122, a display unit 125, a storage unit 123, and a system controller 124. The input unit 121 is a device to input the name of the subject 10, the date of inspection, the scan conditions, and the like. The input unit 121 is, e.g., a keyboard, a pointing device, and a touch panel. The image generator 122 is a device to generate a tomographic image by using the digital data collected with the data collection unit 107. The image generator 122 is, e.g., an MPU or a GPU (Graphics Processing Unit). The display unit 125 is a device to display the tomographic image reconstructed with the image generator 122, or the like. The display unit 125 is, e.g., a liquid crystal display or a touch panel. The storage unit 123 is a device to store the digital data collected with the data collection unit 107, the tomographic image reconstructed with the image generator 122, a program executed with the system controller 124, data used with the program, and the like. The storage unit 123 is, e.g., an HDD (Hard Disk Drive) or an SSD (Solid State Drive). The system controller 124 is a device to control the respective elements, i.e., the gantry controller 108, the bed controller 109, the X-ray controller 110, and the like. The system controller 124 is, e.g., a CPU (Central Processing Unit).

When the high-voltage generator 111 generates a tube voltage as a high voltage applied to the X-ray source 101, based on the scan conditions inputted from the input unit 121 and set, an X-ray corresponding to the scan conditions is emitted from the X-ray source 101 to the subject 10. The X-ray detector 106 detects the X-ray, emitted from the X-ray source 101 and transmitted through the subject 10, with the multiple detection elements, and obtains the spatial distribution of the transmitted X-ray. The rotating plate 102, controlled with the gantry controller 108, rotates based on the scan conditions inputted from the input unit 121, especially based on a rotational speed or the like. The bed 105, controlled with the bed controller 109, operates based on the scan conditions inputted from the input unit 121, especially based on a helical pitch or the like, to relatively move with respect to the rotating plate 102, so as to change a scan position.

With the X-ray emission with the X-ray source 101 and the X-ray detection with the X-ray detector 106, repeated in accordance with the rotation of the rotating plate 102, projection data as an X-ray projection image of the subject 10 is measured at various projection angles. The projection data is associated with "view" (View) representing each projection angle and "channel" (ch) number and a column number as detection element numbers in the X-ray detector 106. The measured projection data is transmitted to the image generator 122. The image generator 122 performs back projection processing on the multiple projection data, to generate a tomographic image. The generated tomographic image is displayed on the display unit 125 or stored in the storage unit 123.

Since the tomographic image is used in diagnosis of the subject 10, it is desirable that the projection data is measured without excess or deficiency with respect to a region of a diagnostic object part. For example, when the measurement range of the projection data is smaller than the region of the diagnostic object part, the diagnosis may be affected, while, when the measurement range is too wide, the amount of ineffective exposure of the subject 10 is increased. Accordingly, in the present embodiment, a scan end position is more accurately determined so as to prevent excess or deficiency of the measurement range of the projection data.

Figure 2:
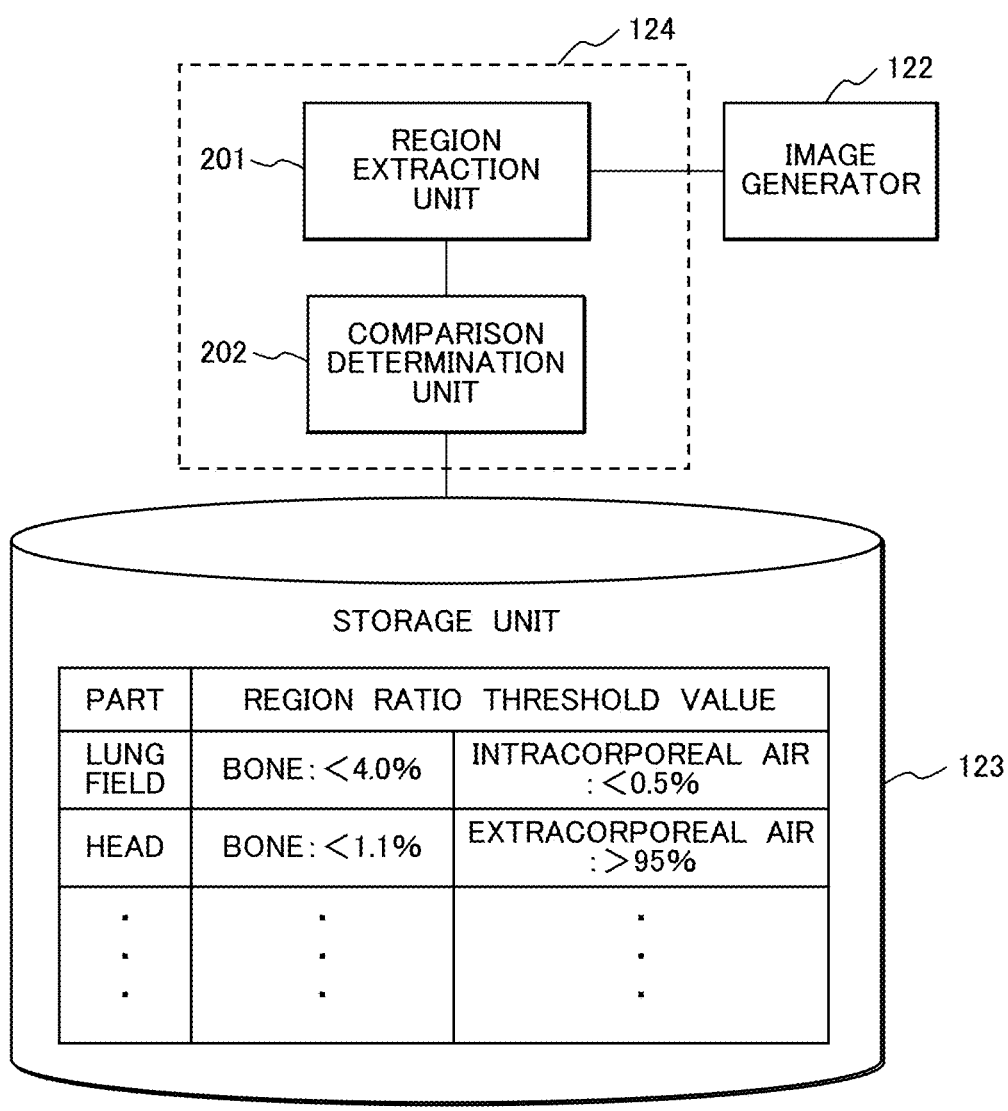
FIG. 2 is a block diagram showing an example of functional blocks according to the first embodiment.

The functional blocks of the present embodiment will be described by using FIG. 2. Note that these functional blocks may be configured with specialized hardware using an ASIC (Application Specific Integrated Circuit), an FPGA (Field-Programmable Gate Array), or the like, or may be configured with software which operates on the system controller 124. In the following description, the functional blocks of the present embodiment are configured with software.

The present embodiment has a region extraction unit 201 and a comparison determination unit 202. Hereinbelow, the respective elements will be described. Note that in the storage unit 123, a region ratio threshold value, previously determined in a scan end position as a position to terminate scanning, is stored for each part subject to scanning. The region ratio threshold value is determined based on statistical data or the like. For example, the region ratio threshold value may be determined in correspondence with gender or age of the subject 10.

The region extraction unit 201 extracts a predetermined region from the tomographic image generated with the image generator 122 during scanning. The extracted region differs depending on scan object part. For example, with respect to a lung field, a bone region and an intracorporeal air region are extracted, and with respect to a head, a bone region and an extracorporeal air region are extracted.

The comparison determination unit 202 determines whether or not the scan position has arrived at the scan end position based on comparison between a region ratio calculated by using the regions extracted with the region extraction unit 201 and the region ratio threshold value stored in the storage unit 123. The threshold value used in the determination of scan end position is read from the storage unit 123 in correspondence with scan object part.

Figure 3:
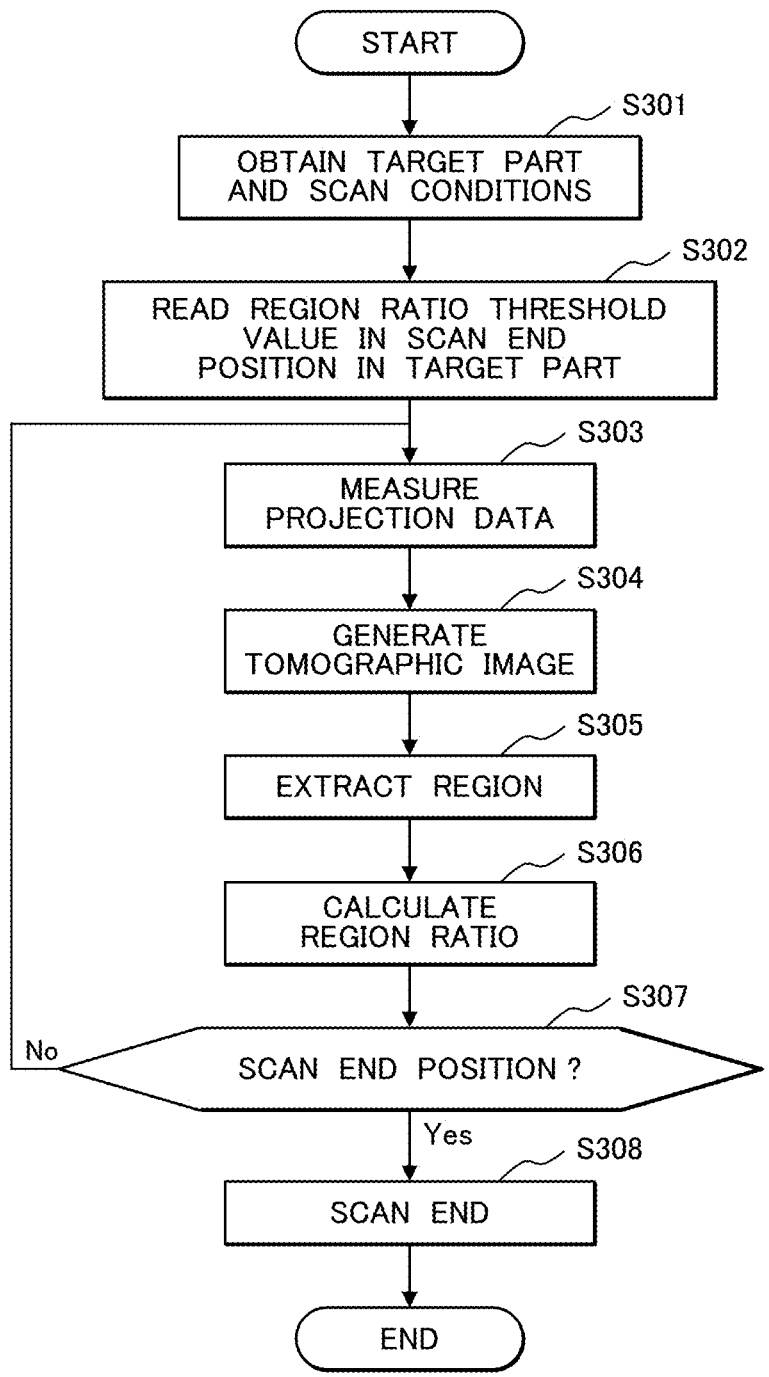
FIG. 3 is a flowchart showing an example of the flow of processing according to the first embodiment.

Next, an example of the flow of processing according to the present embodiment will be described by step by using FIG. 3.

(S301)

The system controller 124 obtains a target part as a part to be the object of scanning and scan conditions. The target part and the scan conditions are inputted by an operator via the input unit 121.

(S302)

The system controller 124 reads a region ratio threshold value in the scan end position with respect to the target part obtained at S301 from the storage unit 123.

(S303)

The system controller 124 causes the scan gantry part 100 to measure the projection data based on the scan conditions obtained at S301. That is, when the rotating plate 102 rotates at a constant speed, the X-ray is emitted from the X-ray source 101 to the subject 10, the X-ray transmitted through the subject 10 is detected with the X-ray detector 106, and the projection data is measured at various projection angles. The measured projection data is transmitted to the image generator 122.

(S304)

The image generator 122 generates a tomographic image in the scan position by using the projection data measured at S303. The generated tomographic image is transmitted to the region extraction unit 201.

(S305)

The region extraction unit 201 extracts a predetermined region, determined in accordance with target part, from the tomographic image generated at S304. For example, when the target part is a lung field, a bone region and an intracorporeal air region are extracted, while, when the target part is a head, a bone region and an extracorporeal air region are extracted. In the tomographic image generated with the X-ray CT apparatus, a CT number for bone, 400 to 1000, and a CT number for air, −1000, are greatly different from a CT number for adipose tissue and soft tissue, −100 to 100. Accordingly, the bone and air regions can be easily extracted.

(S306)

The comparison determination unit 202 calculates a region ratio by using the region extracted at S305.

(S307)

The comparison determination unit 202 compares the region ratio threshold value read at S302 with the region ratio calculated at S306, and determines whether or not the scan position has arrived at the scan end position. When it is determined that the scan position has arrived at the scan end position, the process proceeds to S308. When it is determined that the scan position has not arrived at the scan end position, the process returns to S303. That is, the measurement of the projection data is continued until it is determined that the scan position has arrived at the scan end position.

Figure 4:
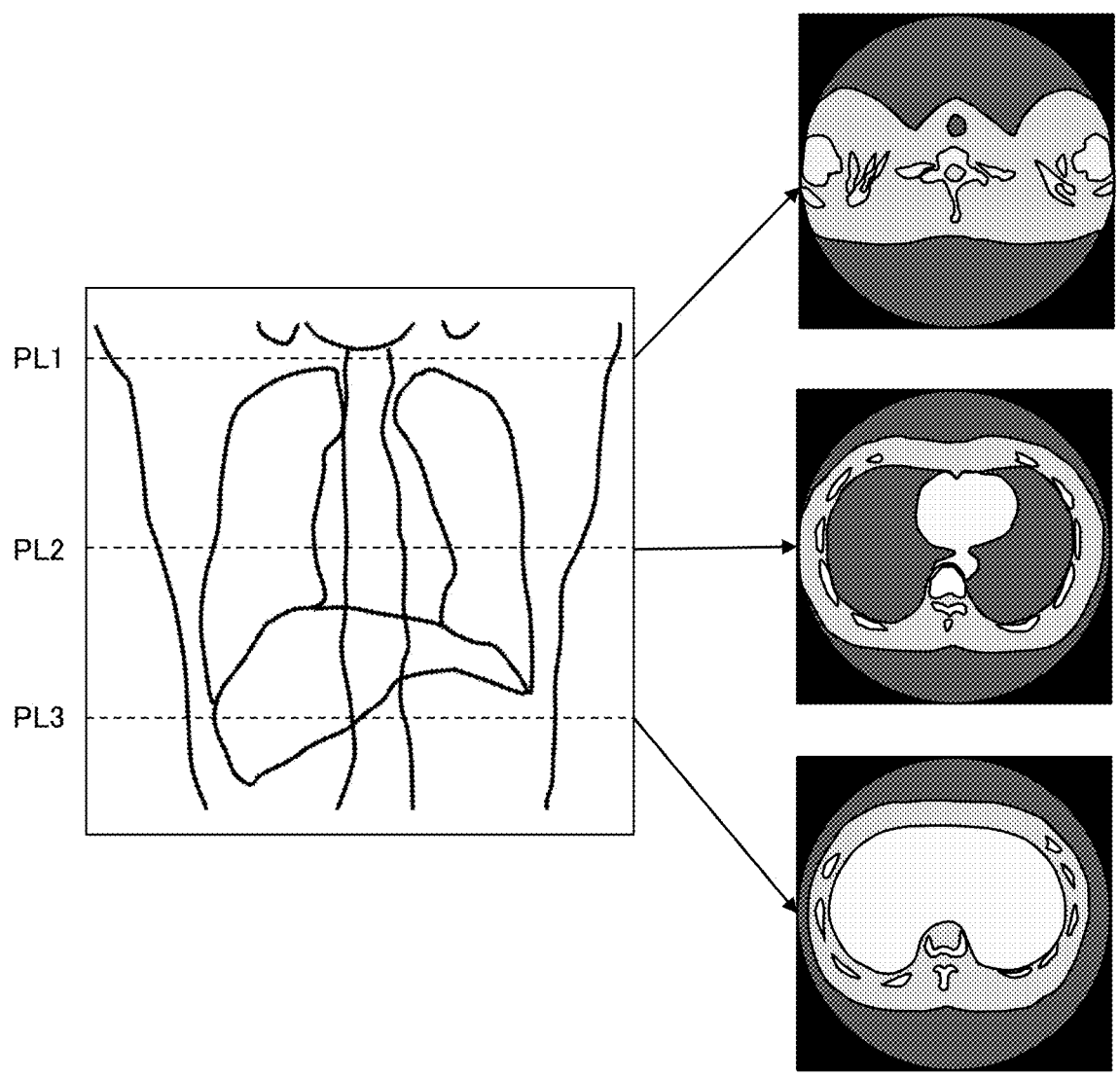
FIG. 4 is an explanatory view of an example of tomographic images in a lung field.

The scan end position determination processing upon scanning of the lung field will be described by using FIGS. 4 and 5. As an example of the tomographic images of the lung field, FIG. 4 shows tomographic images in scan positions PL1, PL2, and PL3. In the scan position PL1 on the head side, the ratio of the bone region is comparatively large, i.e. about 30%. In the scan position PL2 around the center and the scan position PL3 on the lower extremity side, the bone region ratio is about several percent. Further, in the scan position PL2, the ratio of the intracorporeal air region is comparatively large, i.e. about 60%. In the scan positions PL1 and PL3, the ratio of the intracorporeal air region is about several percent.

Figure 5:
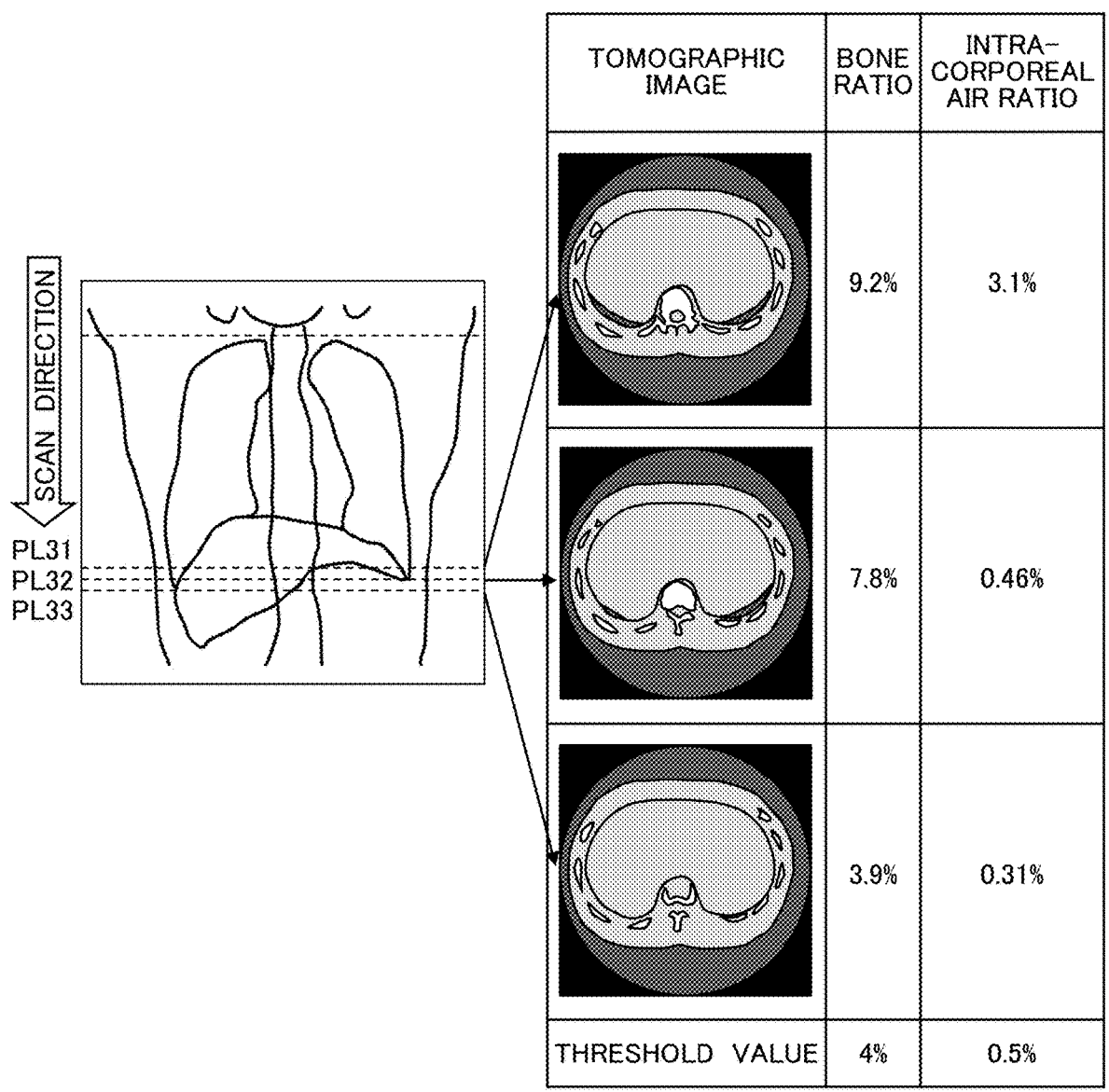
FIG. 5 is an auxiliary explanatory view of scan end position determination processing in the lung field.

FIG. 5 illustrates tomographic images around the scan end position upon scanning of the lung field from the head side, the bone ratios and the intracorporeal air ratios in the respective tomographic images, and the threshold values. The threshold values for the bone ratio and the intracorporeal air ratio are 4% and 0.5%. In the scan position PL31, the bone ratio and the intracorporeal air ratio are 9.2% and 3.1%, i.e., the ratios are larger than the threshold values. Accordingly, it is determined that the scan position has not arrived at the scan end position. In the scan position PL32, the intracorporeal air ratio is 0.46%, i.e., it is smaller than the threshold value 0.5%, however, the bone ratio is 7.8%, i.e., it is larger than the threshold value 4%. Accordingly, it is determined that the scan position has not arrived at the scan end position. In the scan position PL33, the bone ratio is 3.9% and the intracorporeal air ratio is 0.31%, i.e., both ratios are smaller than the threshold values 4% and 0.5%. Accordingly, it is determined that the scan position has arrived at the scan end position.

Figure 6:
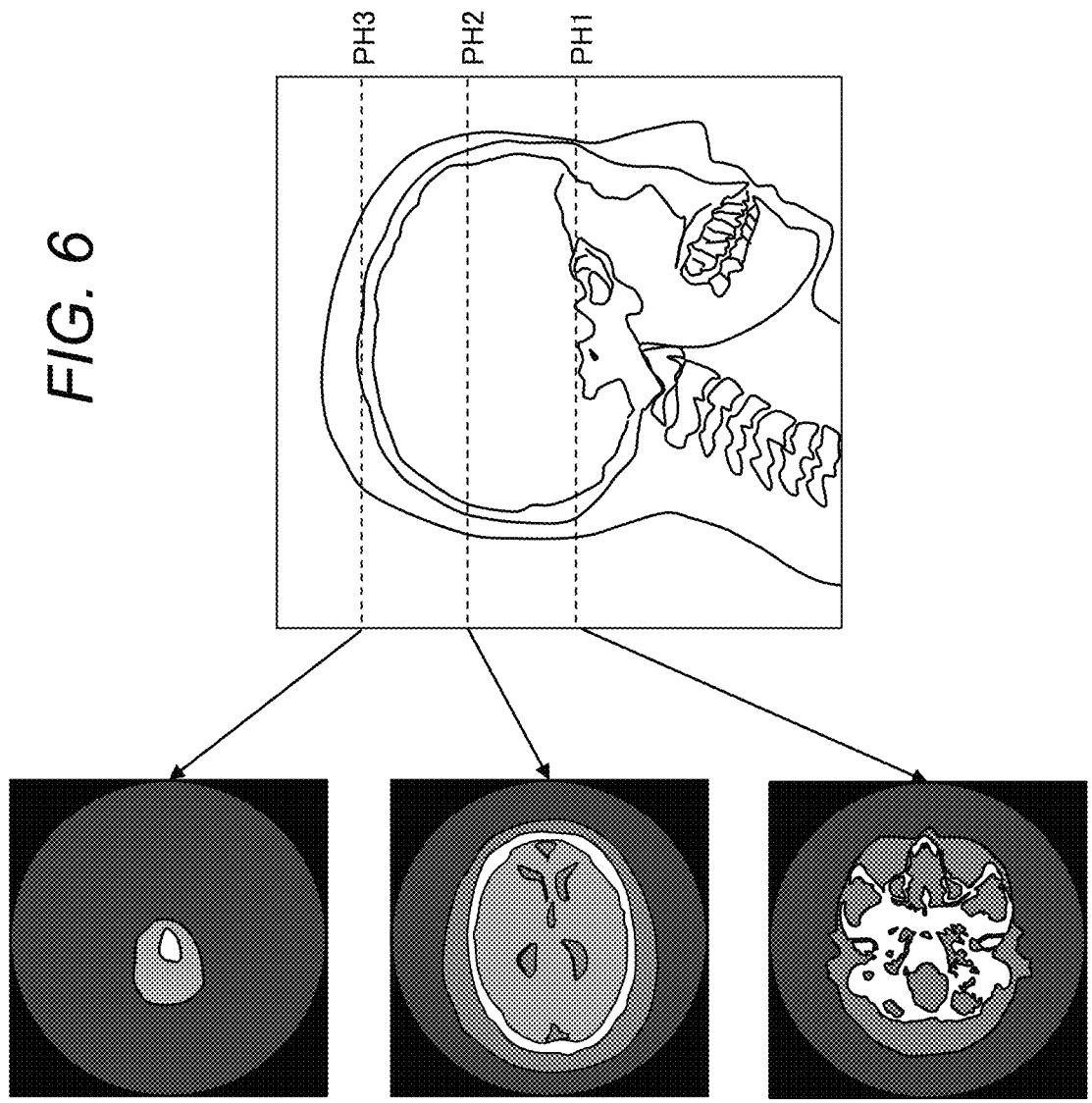
FIG. 6 is an explanatory view of an example of tomographic images in a head.

The scan end position determination processing upon scanning of the head will be described by using FIGS. 6 and 7. As examples of the tomographic images of the head, FIG. 6 shows tomographic images in scan positions PH1, PH2 and PH3. The ratio of the bone region decreases from the scan position PH1 around the orbits through the scan position PH2 around the center to the scan position PH3 around the parietal part. The ratio of the extracorporeal air also decreases from the scan position PH1 through the scan position PH2 to the scan position PH3.

Figure 7:
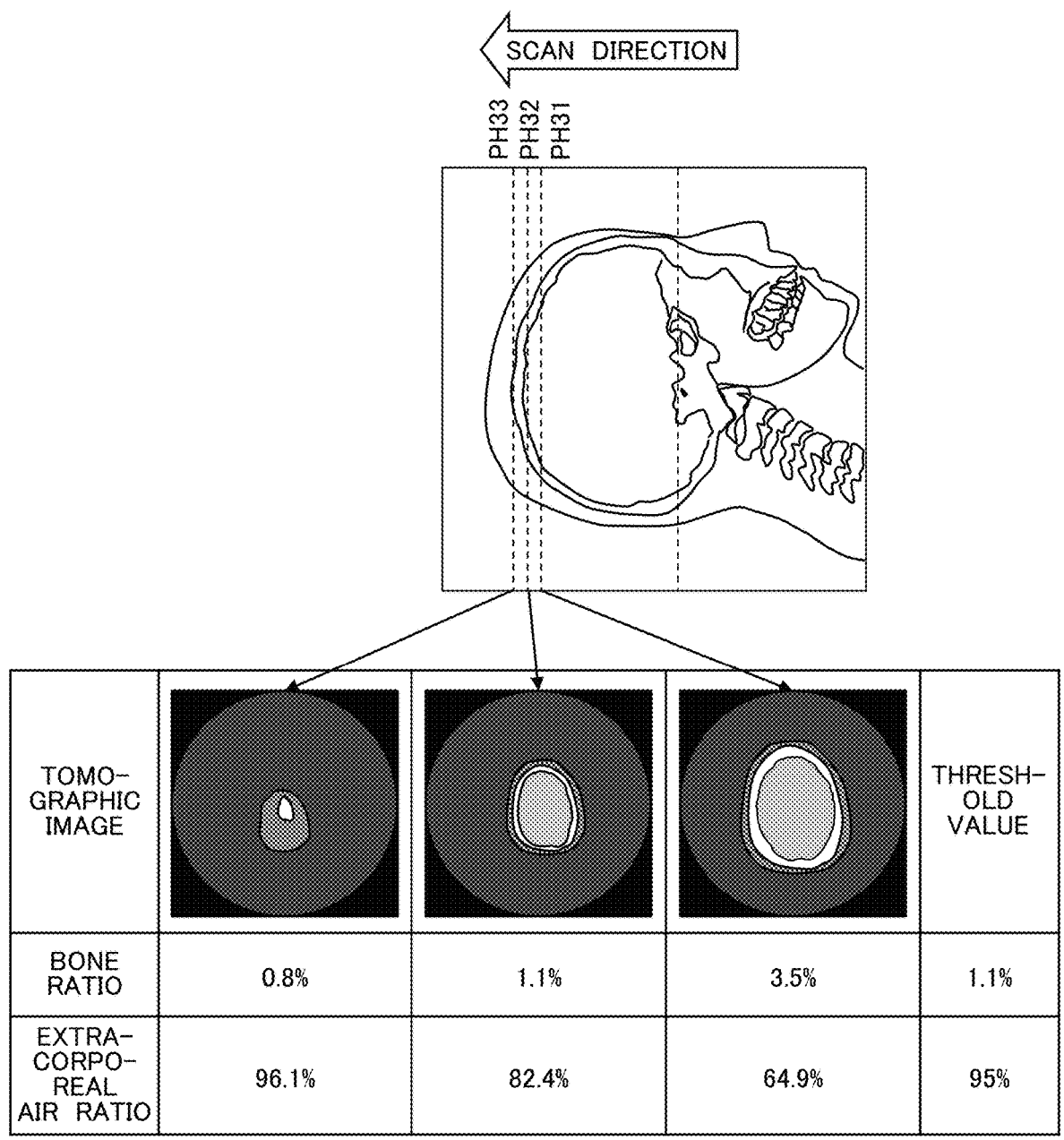
FIG. 7 is an auxiliary explanatory view of the scan end position determination processing in the head.

FIG. 7 illustrates tomographic images around the scan end position upon scanning of the head from around the orbits to the parietal part, the bone ratios and the intracorporeal air ratios in the respective tomographic images, and the threshold values. The threshold values for the bone ratio and the extracorporeal air ratio are 1.1% and 95%. In the scan position PH31, the bone ratio and the extracorporeal air ratio are 3.5% and 64.9%, i.e., the ratios do not satisfy the threshold values. Accordingly, it is determined that the scan position has not arrived at the scan end position. In the scan position PH32, the bone ratio is 1.1%, i.e., it satisfies the threshold value, however, the extracorporeal air ratio is 82.4%, i.e., it does not satisfy the threshold value. Accordingly, it is determined that the scan position has not arrived at the scan end position. In the scan position PH33, the bone ratio is 0.8% and the extracorporeal air is 96.1%, i.e., both ratios satisfy the threshold values. Accordingly, it is determined that the scan position has arrived at the scan end position.

(S308)

The system controller 124 terminates the scanning in the scan gantry part 100. That is, the X-ray emission from the X-ray source 101 to the subject 10 and the rotation of the rotating plate 102 are stopped, and the flow of processing ends.

With the above-described flow of processing, based on the ratios of the bone region and the intracorporeal/extracorporeal air region extracted from the tomographic image generated during scanning, it is determined whether or not the scan position has arrived at the scan end position. Accordingly, it is possible to more accurately determine the scan end position. Especially, even in the case of a part deeper from the X-ray source 101, the part is not unclear on the tomographic image, and the degradation of the accuracy of the scan end position determination is prevented. Further, as it is possible to more accurately determine the scan end position, extra scanning can be avoided, thus it is possible to reduce scan time and reduce exposure of the subject 10.

Second Embodiment

Figure 8:
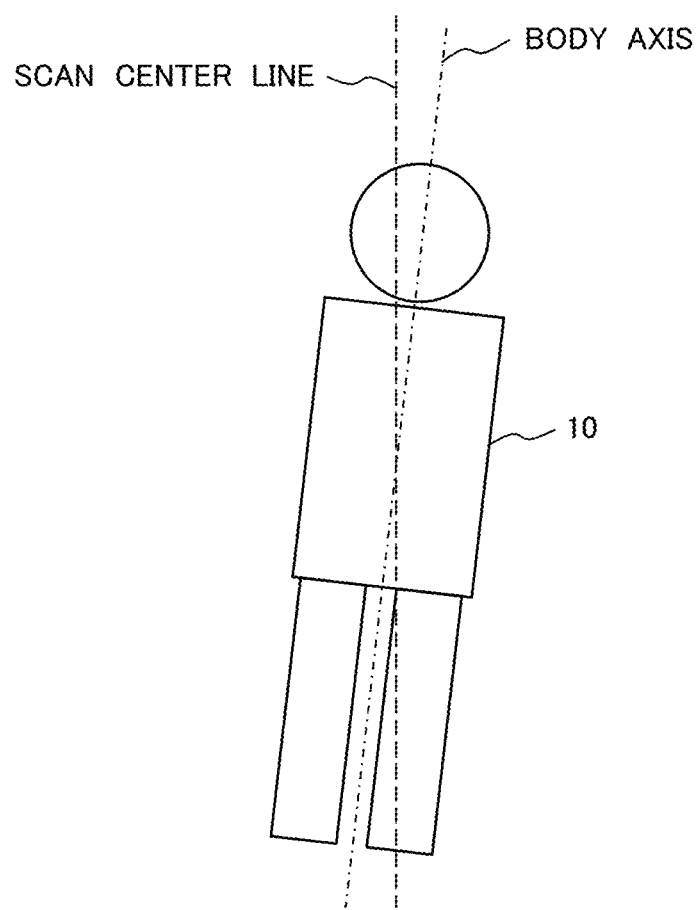
FIG. 8 is an explanatory view of body axis tilt of a subject with respect to a scan center line.

In the first embodiment, the scan end position is determined by comparing the ratio of a predetermined region extracted from a tomographic image generated during scanning with a previously-determined threshold value. The threshold value in the scan end position is determined in a cross section orthogonal to the body axis of the subject 10. As shown in FIG. 8, when the body axis of the subject 10 is tilted with respect to a scan center line as a rotation axis of the rotating plate 102, the accuracy of the scan end position determination is lowered in some cases. Accordingly, in the present embodiment, more accurate determination of the scan end position, even when the body axis of the subject 10 is tilted with respect to the scan center line, will be described. Note that in the present embodiment, since some of the constituent elements and functions described in the first embodiment can be applied, explanation of similar constituent elements and functions will be omitted.

Figure 9:
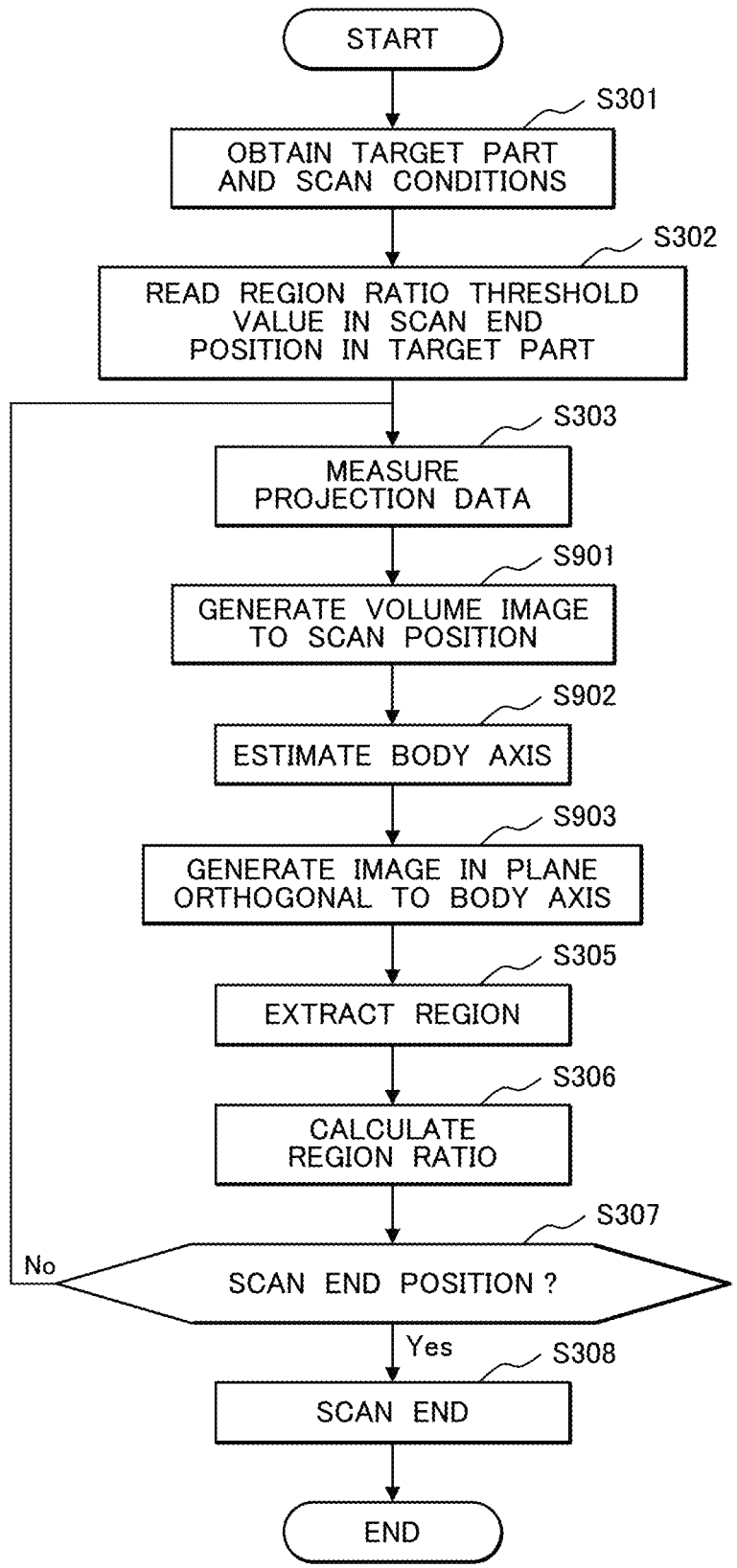
FIG. 9 is a flowchart showing an example of the flow of processing according to a second embodiment of the present invention.

An example of the flow of processing according to the present embodiment will be described by step by using FIG. 9. Note that the difference between FIG. 3 showing the example of the flow of processing according to the first embodiment and FIG. 9 is that S901 to S903 are added in place of the tomographic image generation processing at S304. Hereinbelow, the processing at S901 to S903 will be mainly described.

(S301) to (S303)

The processing at S301 to S303 is the same as the processing at S301 to S303 according to the first embodiment.

(S901)

The image generator 122 generates a volume image to the scan position by using the projection data measured at S303. The volume image is generated by stacking multiple tomographic images in a scan direction.

(S902)

The image generator 122 estimates the body axis of the subject 10 by using the volume image generated at S901. The body axis may be estimated by any processing. For example, the body axis may be estimated by using a core line obtained by thinning the spinal column extracted from the volume image.

(S903)

The image generator 122 generates an image in a plane orthogonal to the body axis estimated at S902. The image in the plane orthogonal to the body axis is generated by using the volume image generated at S901. The generated image is transmitted to the region extraction unit 201.

(S305)

The region extraction unit 201 extracts a predetermined region determined in correspondence with target part from the image generated at S903.

(S306) to (S308)

The processing at S306 to S308 is the same as the processing at S306 to S308 according to the first embodiment.

With the flow of processing as described above, even when the body axis of the subject 10 is tilted with respect to the scan center line, the scan end position is determined based on a predetermined region extracted from an image generated in a plane orthogonal to the body axis. Accordingly, the degradation of the accuracy of the scan end position determination is prevented.

Figure 10:
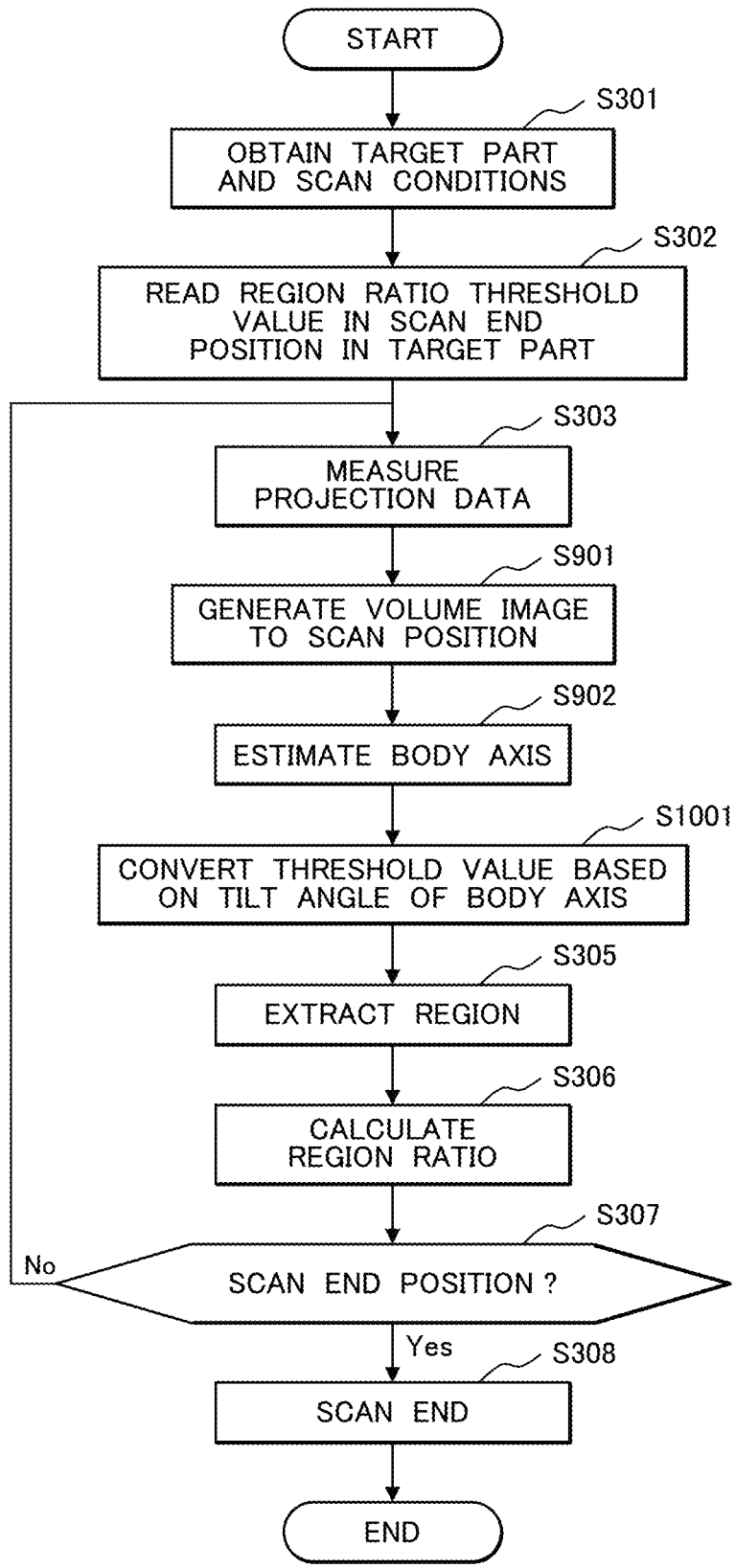
FIG. 10 is a flowchart showing another example of the flow of processing according to the second embodiment.

Next, another example of the flow of processing according to the preset embodiment will be described by step by using FIG. 10. Note that the difference between FIG. 9 showing the example of the flow of processing according to the present embodiment and FIG. 10 is that S1001 is added in place of the image generation in the plane orthogonal to the body axis at S903. Hereinbelow, the processing at S1001 will be mainly described.

(S301) to (S303)

The processing at S301 to S303 is the same as the processing at S301 to S303 according to the first embodiment.

(S901) to (S902)

The processing at S901 to S902 is the same as the processing at S901 to S902 described by using FIG. 9.

(S1001)

The image generator 122 calculates a tilt angle between the body axis estimated at S902 and the scan center line. Further, the threshold value, read at S302 in correspondence with the calculated tilt angle, is converted with the comparison determination unit 202.

(S305)

The region extraction unit 201 extracts a predetermined region determined in correspondence with target part, from a tomographic image in a scan position in the volume image generated at S901.

(S306)

The processing at S306 is the same as the processing at S306 according to the first embodiment.

(S307)

The comparison determination unit 202 compares the threshold value converted at S1001 with the region ratio calculated at S306, to determine whether or not the scan position has arrived at the scan end position. When it is determined that the scan position has arrived at the scan end position, the process proceeds to S308. When it is determined that the scan position has not arrived at the scan end position, the process returns to S303.

(S308)

The processing at S308 is the same as the processing according at S308 according to the first embodiment.

With the flow of processing as described above, even when the body axis of the subject 10 is tilted with respect to the scan center line, the scan end position is determined based on a threshold value converted in correspondence with the tilt angle of the body axis. Accordingly, the degradation of the accuracy of the scan end position determination is prevented. In the flow of processing shown in FIG. 10, since the image generation in the plane orthogonal to the estimated body axis can be omitted, it is possible to perform the processing at a higher speed in comparison with FIG. 9.

Third Embodiment

In the first embodiment, the scan end position is determined by comparing the ratio of a predetermined region extracted from a tomographic image generated during scanning with a previously determined threshold value. The threshold value in the scan end position is determined on the assumption that the part of the subject 10 stands still. With respect to a part which moves during scanning such as a heart, the accuracy of the scan end position determination is lowered in some cases. Accordingly, in the present embodiment, more accurate scan end position determination, even when the part of the subject 10 moves, will be described.

Note that in the present embodiment, since some of the constituent elements and functions described in the first embodiment can be applied, explanation of similar constituent elements and functions will be omitted.

Figure 11:
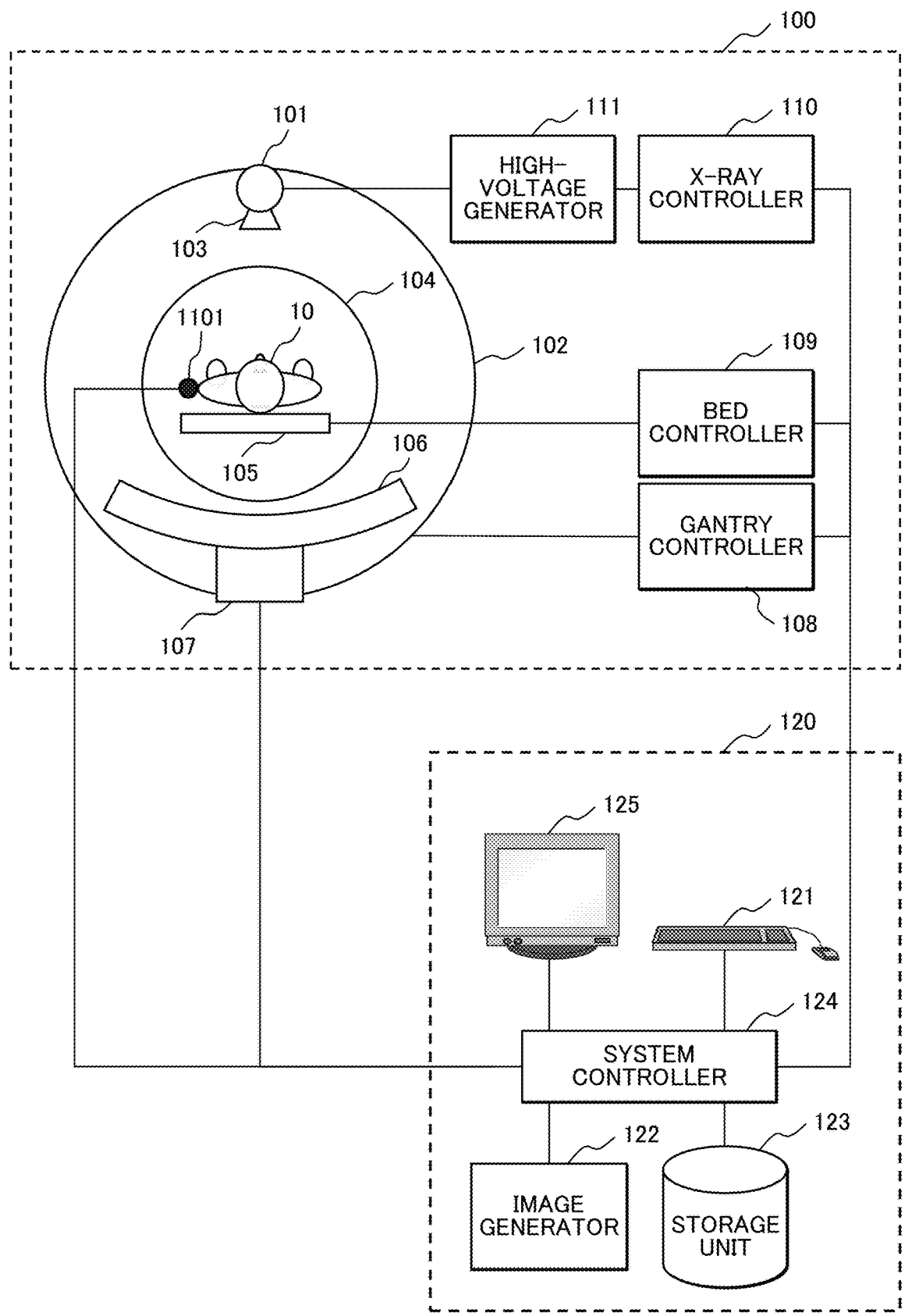
FIG. 11 is a block diagram showing an example of the entire configuration of the X-ray CT apparatus according to a third embodiment of the present invention.

The entire configuration of the X-ray CT apparatus according to the present embodiment will be described by using FIG. 11. Note that the difference between FIG. 1 illustrating the entire configuration of the first embodiment and FIG. 11 is that an electrocardiographic waveform measurement section 1101 is added. The electrocardiographic waveform measurement section 1101 is a device to measure an electrocardiographic waveform indicating electrical action of the heart of the subject 10. The electrocardiographic waveform is a periodical graph in which a lateral axis indicates a heart phase. The electrocardiographic waveform measurement section 1101 is controlled with the system controller 124 as in the case of the other elements.

Figure 12:
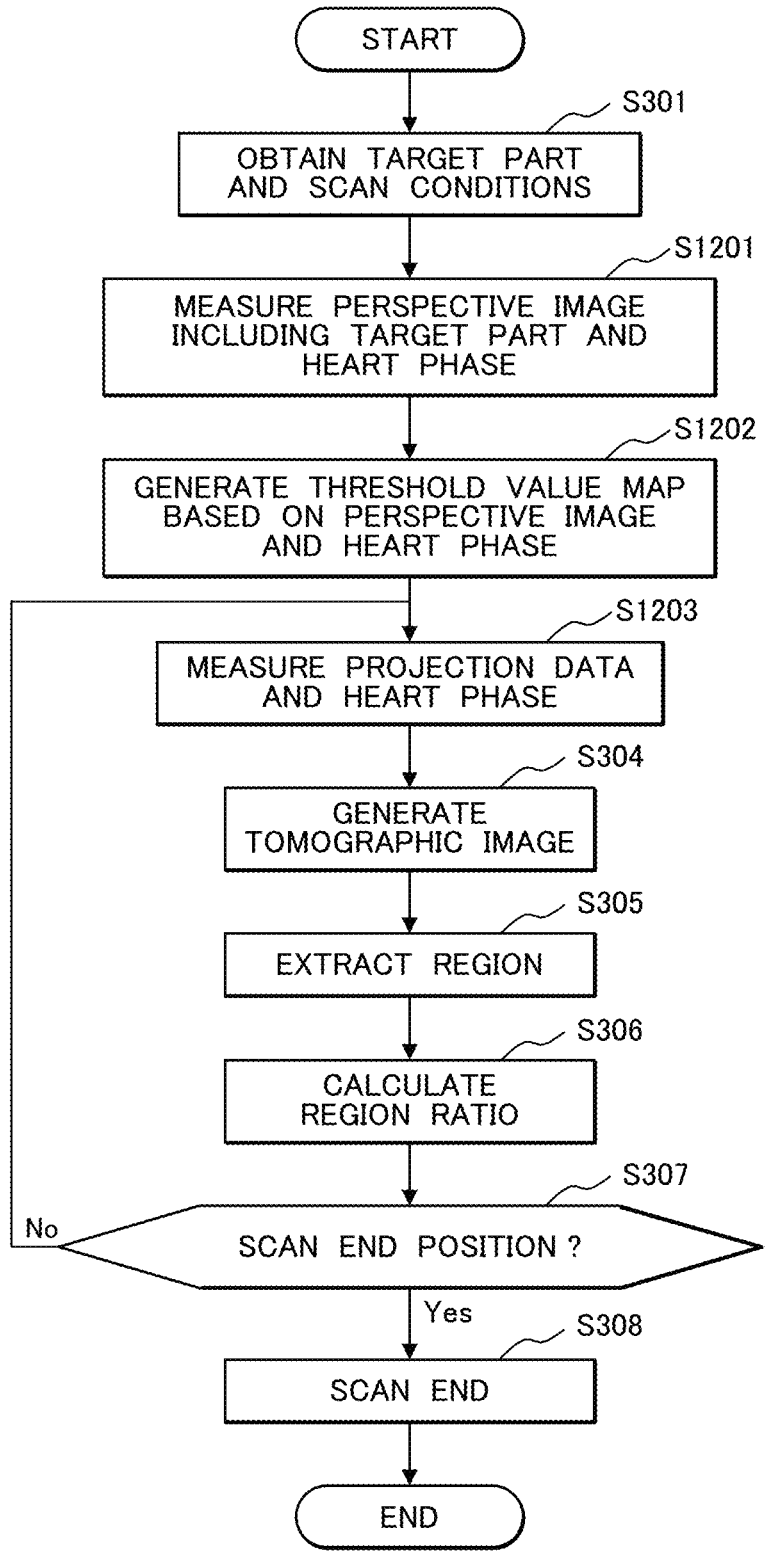
FIG. 12 is a flowchart showing an example of the flow of processing according to the third embodiment.

An example of the flow of processing according to the present embodiment will be described by step by step using FIG. 12. Note that the difference between FIG. 3 showing the example of the processing according to the first embodiment and FIG. 12 is that S1201 to S1203 are added in place of the threshold reading processing at S302 and the projection data measurement processing at S303. Hereinbelow, the processing at S1201 to S1203 will be mainly described.

(S301)

The system controller 124 obtains a target part as a part to be the object of scanning and scan conditions. The target part in the present embodiment is a part which periodically moves during scanning, e.g., a heart.

(S1201)

The system controller 124 causes the scan gantry part 100 to measure a perspective image including the target part, and causes the electrocardiographic waveform measurement section 1101 to measure heart phases upon measurement of the perspective image.

Figure 13:
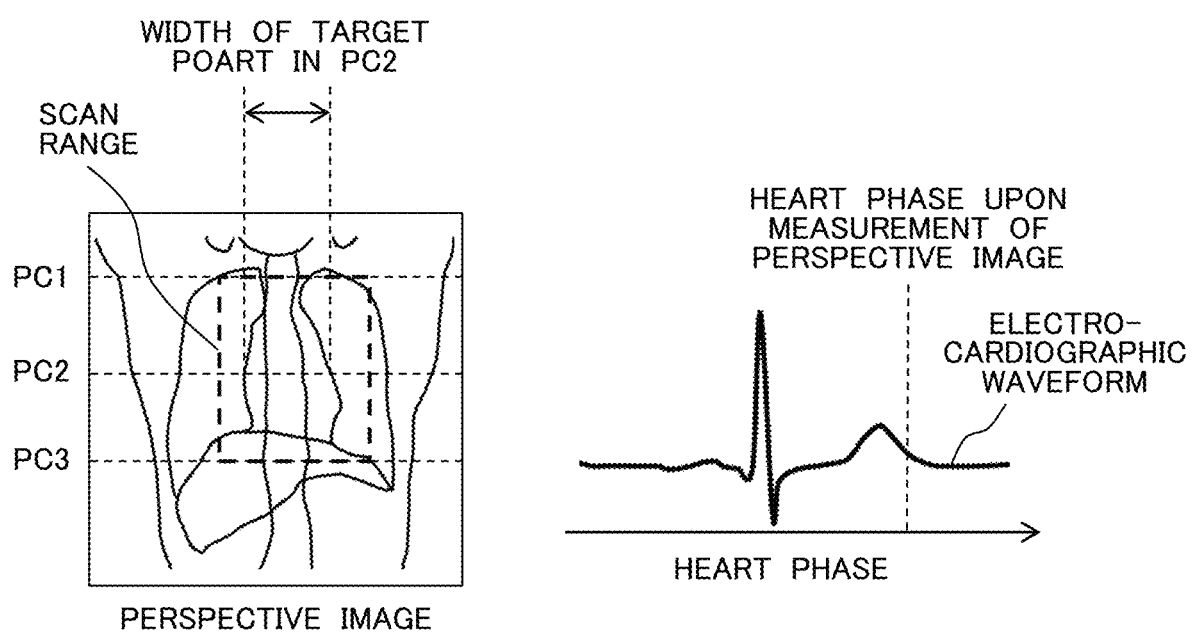
FIG. 13 is an auxiliary explanatory view of processing of measuring a perspective view including a target part and a heart phase.

The perspective image and the heart phases measured at the present step will be described by using FIG. 13. The perspective image is measured by emitting the X-ray from the X-ray source 101 to the subject 10 while the bed 105 is moved along the rotation axis of the rotating plate 102 in a state where the rotating plate 102 is stopped, and detecting the X-ray transmitted through the subject 10 with the x-ray detector. The heart moves periodically during the measurement of the perspective image, and the size of the heart changes in correspondence with heart phase. By measuring the heart phases upon measurement of the perspective image, the heart width in each scan position in the perspective image can be associated with a corresponding heart phase.

The comparison determination unit 202 generates a threshold value map based on the perspective image and the heart phases measured at S1201. The threshold value map shows threshold values determined for the respective heart phases in the respective scan positions.

Figure 14:
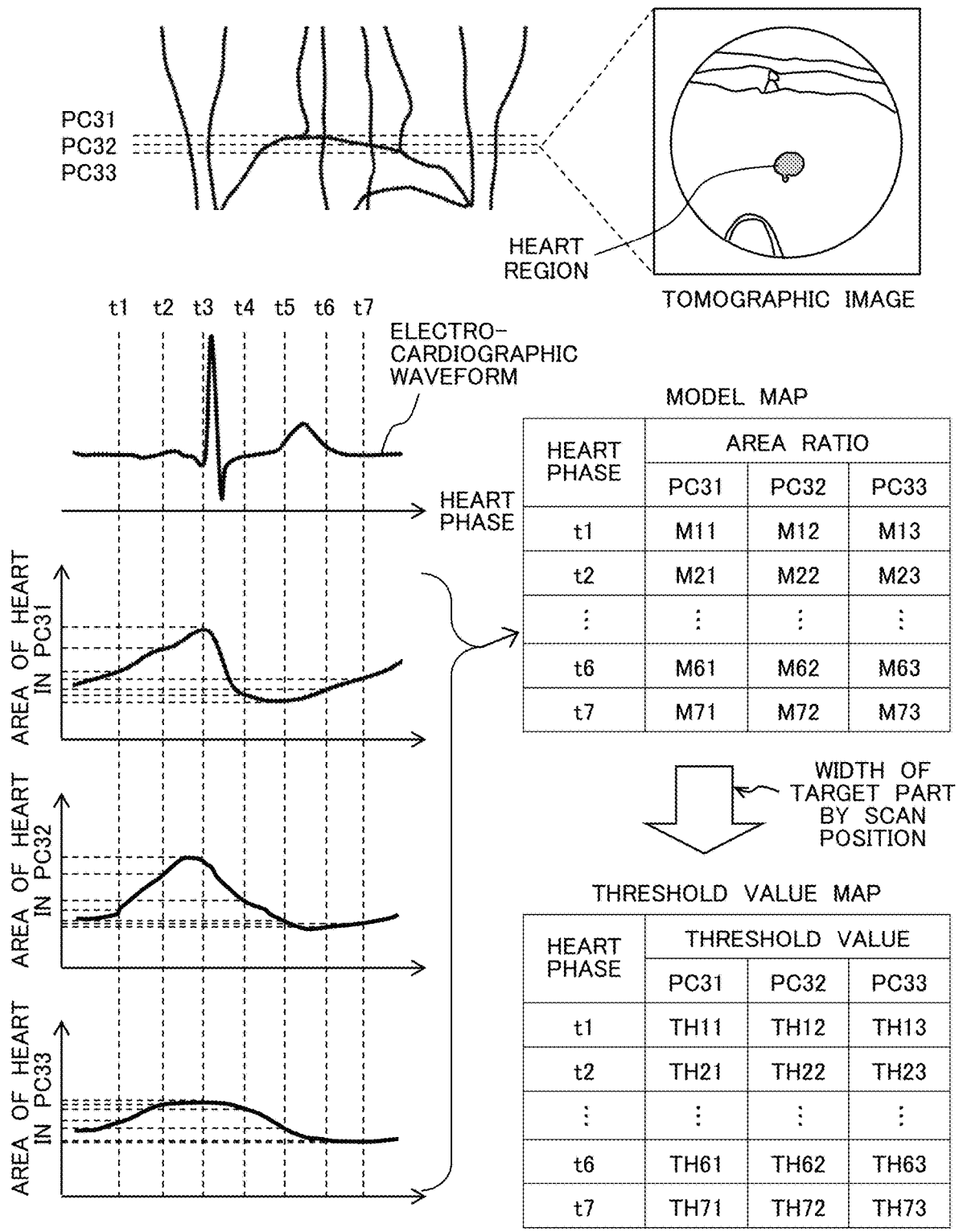
FIG. 14 is an auxiliary explanatory view of processing of generating a threshold value map.

The threshold value map generated at the present step will be described by using FIG. 14. The size of the part which periodically moves, e.g., the heart, differs by heart phase in each scan position. The area of the heart region in the tomographic image changes in correspondence with heart phase. For example, as shown in a graph of FIG. 14, the area of the heart region in the respective scan positions PC31 to PC33 changes in correspondence heart phases t1 to t7, and the way of change differs in accordance with scan position. Accordingly, in the present embodiment, a model map showing area ratios for the respective heart phases in the respective scan positions is previously stored in the storage unit 123. The area ratio is a value obtained by e.g. obtaining a ratio with respect to a minimum area in each scan position, and normalizing the obtained ratio by scan position. Note that the model map may be determined based on statistical data or the like, and may be determined in correspondence with, e.g., gender or age of the subject 10. Further, the number of scan positions and the number of heart phases included in the model map are not limited to three or seven as illustrated in FIG. 14. It is desirable that more heart phases and more scan positions are included for improvement of determination accuracy.

The threshold value map is generated based on the model map read from the storage unit 123, and the perspective image and the heart phases measured at S1201. That is, based on the width of the target part in each scan position obtained from the perspective image and the heart phase upon measurement of the perspective image, the area ratio in each scan position of the model map is converted into a threshold value in each scan position of the threshold value map. The generated threshold value map is stored in the storage unit 123.

(S1203)

The system controller 124 causes the scan gantry part 100 to measure the projection data based on the scan conditions obtained at S301, and causes the electrocardiographic waveform measurement section 1101 to measure the heart phase upon measurement of the projection data. The measured projection data is transmitted to the image generator 122. The measured heart phase is transmitted to the comparison determination unit 202.

(S304) to (S306)

The processing at S304 to S306 is the same as the processing at S304 to S306 according to the first embodiment.

(S307)

The comparison determination unit 202 reads a threshold value in the scan position by using the heart phase measured at S1203 from the threshold value map generated at S1201. The comparison determination unit 202 compares the read threshold value with the area ratio calculated at S306, to determine whether or not the scan position has arrived at the scan end position. When it is determined that the scan position has arrived at the scan end position, the process proceeds to S308. When it is determined that the scan position has not arrived at the scan end position, the process returns to S1203.

(S308)

The processing at S308 is the same as the processing at S308 according to the first embodiment.

With the flow of processing as described above, even when the part of the subject 10 moves, the scan end position is determined based on a threshold value set in correspondence with the phase of the movement. Accordingly, the degradation of the accuracy of the scan end position determination is prevented.

As described above, the multiple embodiments regarding the X-ray CT apparatus according to the present invention have been explained. The X-ray CT apparatus according to the present invention is not limited to the above-described embodiments, but may be embodied with modification of the constituent elements within a range not departing from the subject matter of the invention. Further, the plural constituent elements disclosed in the above-described embodiments may be arbitrarily combined. For example, the second embodiment and the third embodiment may be combined. Further, some constituent elements may be deleted from all the constituent elements shown in the above-described embodiments.

REFERENCE SIGNS LIST

10: subject, 100: scan gantry part, 101: X-ray source, 102: rotating plate, 103: collimator, 104: opening, 105: bed, 106: X-ray detector, 107: data collection unit, 108: gantry controller, 109: bed controller, 110: X-ray controller, 111: high-voltage generator, 120: operation unit, 121: input unit, 122: image generator, 123: storage unit, 124: system controller, 125: display unit, 201: region extraction unit, 202: comparison determination unit, 1101: electrocardiographic waveform measurement section

What is claimed is:

1. An X-ray CT apparatus comprising:
a rotating plate that rotates an X-ray source to emit an X-ray to a subject and an X-ray detector, oppositely provided to the X-ray source, to detect the X-ray transmitted through the subject, around the subject;
a bed that the subject is placed on, and that relatively moves with respect to the rotating plate, to change a scan position;
an image generator that generates a tomographic image in the scan position based on output from the X-ray detector;
a storage unit that holds a region ratio threshold value previously determined in a scan end position;
a region extraction unit that extracts a predetermined region from the tomographic image generated during scanning; and
a comparison determination unit that determines whether or not the scan position has arrived at the scan end position based on comparison between a region ratio calculated by using the region and the threshold value,
wherein the image generator generates a volume image to the scan position, and calculates a tilt angle of a body axis of the subject, estimated by using the volume image, and
wherein the comparison determination unit determines whether or not the scan position has arrived at the scan end position by using a threshold value converted based on the tilt angle.

2. The X-ray CT apparatus according to claim 1,
wherein the storage unit holds respective threshold values for a bone and intracorporeal air as threshold values for a lung field, and
wherein the region extraction unit extracts the bone and the intracorporeal air from the tomographic image generated during scanning.

3. The X-ray CT apparatus according to claim 1,
wherein the storage unit holds respective threshold values for a bone and extracorporeal air as threshold values for a head, and
wherein the region extraction unit extracts the bone and the extracorporeal air from the tomographic image generated during scanning.

4. The X-ray CT apparatus according to claim 1,
wherein the image generator generates a volume image to the scan position, and generates an image in a plane orthogonal to a body axis of the subject, estimated by using the volume image, and
wherein the region extraction unit extracts a region from the image.

5. An X-ray CT apparatus comprising:
a rotating plate that rotates an X-ray source to emit an X-ray to a subject and an X-ray detector, oppositely provided to the X-ray source, to detect the X-ray transmitted through the subject, around the subject;
a bed that the subject is placed on, and that relatively moves with respect to the rotating plate, to change a scan position;
an image generator that generates a tomographic image in the scan position based on output from the X-ray detector;
a storage unit that holds a region ratio threshold value previously determined in a scan end position;
a region extraction unit that extracts a predetermined region from the tomographic image generated during scanning;
a comparison determination unit that determines whether or not the scan position has arrived at the scan end position based on comparison between a region ratio calculated by using the region and the threshold value; and
an electrocardiographic waveform measurement section that measures a heart phase upon scanning of the subject,
wherein the comparison determination unit determines whether or not the scan position has arrived at the scan end position by using a threshold value obtained from a threshold value map, in which a threshold value by heart phase is determined in each scan position, by using the heart phase upon scanning.

6. The X-ray CT apparatus according to claim 5,
wherein the storage unit further holds a model map showing an area ratio by heart phase in each scan position, and
wherein the threshold value map is generated based on a perspective image obtained prior to scanning of the subject, the heart phase upon acquisition of the perspective image, and the model map.

7. A control method for controlling an X-ray CT apparatus, the apparatus including:
a rotating plate that rotates an X-ray source to emit an X-ray to a subject and an X-ray detector, oppositely provided to the X-ray source, to detect the X-ray transmitted through the subject, around the subject;
a bed that the subject is placed on, and that relatively moves with respect to the rotating plate, to change a scan position; and
an image generator that generates a tomographic image in the scan position based on output from the X-ray detector,
the method comprising:
extracting a predetermined region from the tomographic image generated during scanning; and
determining whether or not the scan position has arrived at a scan end position based on comparison between a region ratio calculated by using the region and a region ratio threshold value previously determined in the scan end position,
wherein the image generator generates a volume image to the scan position, and calculates a tilt angle of a body axis of the subject, estimated by using the volume image, and
wherein the comparison determination unit determines whether or not the scan position has arrived at the scan end position by using a threshold value converted based on the tilt angle.

* * * * *